(12) United States Patent
Thakker et al.

(10) Patent No.: US 6,312,917 B1
(45) Date of Patent: Nov. 6, 2001

(54) METHOD OF SCREENING CANDIDATE COMPOUNDS FOR SUSCEPTIBILITY TO OXIDATIVE METABOLISM

(75) Inventors: Dhiren R. Thakker, Raleigh, NC (US); Cuiping Chen, Wallingford, CT (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 09/205,762

(22) Filed: Dec. 4, 1998

(51) Int. Cl.[7] .............................. C12Q 1/26; C12Q 1/28; G01N 33/53
(52) U.S. Cl. ............................ 435/25; 435/28; 435/7.91; 435/7.95
(58) Field of Search ......................... 435/25, 192, 288.4, 435/7.91, 7.95, 28

(56) References Cited

U.S. PATENT DOCUMENTS 4,341,868 * 7/1982 Nakanishi et al. ................... 435/191

FOREIGN PATENT DOCUMENTS

| 0016845 | 10/1980 | (EP) . |
|---|---|---|
| WO95/25175 | 9/1995 | (WO) . |
| WO97/39352 | 10/1997 | (WO) . |
| WO00/22158 | 4/2000 | (WO) . |

OTHER PUBLICATIONS

Ding et al. Purification and characterization of cytochrome P450 2E2 from hepatic microsomes of neonatal rabbits. Arch. Biochem. Biophys. 291 (2), pp. 270–276, (Dec. 1991).*
Nutter et al. Cellular biochemical determinants modulating the metabolism of estrone 3,4–quinone. Chem. Res. Toxicology. 7 (5), pp. 609–613, (Sep. Oct./1994).*
Shet et al. The effects of cytochrome b5, NADPH–P450 reductase, and lipid on the rate of 6β–hydroxylation of testosterone as catalyzed by a human P450 3A4 fusion protein. Arch. Biochem. Biophys. 318 (2), pp. 314–321, (Apr. 1995).*
Ghosh et al., "NADPH–Initiated Cytochrome P450–Dependent Free Iron–Independent Microsomal Lipid Peroxidation: Specific Prevention by Ascorbic Acid," Mol Cell Biochem., vol. 166 (No. 1–2), p. 35–44, (Jan. 30, 1997).
Bondy et al., "Contribution of Hepatic Cytochrome P450 Systems to the Generation of Reactive Oxygen Species," Biochem Pharmacol., vol. 48, (No. 1), p. 155–159, (Jul. 5, 1994).
Puntarulo et al., "Role of Cytochrome P–450 in the Stimulation of Microsomal Production of Reactive Oxygen Species by Ferritin," Biochimica et Biophysica Acta, p. 238–246, (Jul. 30, 1996).
Valerino et al., "Xanthine Oxidase–Mediated Oxidation of Epinephrine," Biochem Pharmacol., p. 47–55, (Jul. 30, 1971).
Ahmed et al., "Oxygen Radical Formation Due to the Effect of Varying Hydrogen Ion Concentrations on Cytochrome P450–Catalyzed Cyclosporine Metabolism in Rat and Human Liver Microsomes," Adv. Exp. Med. Bibl., p. 135–138, (Jul. 30, 1996).
White et al., "Oxygen Activation of Cytochrome P–450," Ann. Rev. Biochem., p. 315–356, (Jul. 30, 1980).
McKillop et al., "The Metabolism and Binding of Catecholamines by teh Hepatic Microsomal Mixed–Function Oxidase of the Rat," Biochem J., p. 135–140, (Jul. 30, 1976).
Puntarulo et al., "Chemiluminescence Studies on the Generation of Oxygen Radicals from the Interaction of NADPH–Cytochrome P–450 Reductase with Iron," Archives of Biochemistry and Biophysics, vol. 258 (No. 2), p. 510–518, (Nov. 1, 1987).
Guengerich, "Catalytic Selectivity of Human Cytochrome P450 Enzymes: Relevance to Drug Metabolism and Toxicity," Toxicology Letters, p. 133–138, (Jul. 30, 1994).
Donato et al., "A Microassay for Measuring Cytochrome P450IA1 and P450IIA1 Activities in Intact Human and Rat Hepatocytes Cultures on 96–Well Plates," Analytical Biochemistry, p. 29–33, (Jul. 30, 1993).
Chrzanowska–Lightowlers et al., "A Microtiter Plate Assay for Cytochrome c Oxidase in Permeabilized Whole Cells," Analytical Biochemistry, p. 45–49, (Jul. 30, 1993).
Buters et al., "A Highly Sensitive Tool for the Assay of Cytochrome P450 Enzyme Activity in Rat, Dog and Man," Biochem Pharmacol., vol. 46, (No. 9), p. 1577–1584, (Jul. 30, 1993).
F. Heinz et al., "A New Spectrophotometric Assay for Enzymes of Purine Metabolism," Enzyme, p. 239–246, (1979).
Ferrer et al., "Fluorescence Detection of Enzymatially Formed Hydrogen Peroxide in Aqueous Solution and in Reversed Micelles," Analytical Biochemistry, p. 129–132, (1990).
XP–002139100, Derwent Accession No. 1989–029589, Patent Number JP63304998 A, Abstract only. (1989).

* cited by examiner

Primary Examiner—Marianne P. Allen
Assistant Examiner—Marjorle A. Moran
(74) Attorney, Agent, or Firm—Jenkins & Wilson, P.A.

(57) ABSTRACT

A method of screening a candidate compound for susceptibility to metabolism by a selected enzyme. The method includes the steps of reacting the candidate compound, an indicator compound precursor and the selected enzyme, the enzyme characterized as having a side reaction associated with metabolic activity of the enzyme wherein a chemical species capable of reacting with the indicator compound precursor is produced; and detecting an indicator compound, the indicator compound produced from the indicator compound precursor by reaction with the chemical species produced from the side reaction associated with metabolic activity of the enzyme, the detection of the indicator compound indicating the susceptibility of the candidate compound to metabolism by the enzyme. A preferred example of the selected enzyme is a cytochrome P450 (CYP).

16 Claims, 10 Drawing Sheets

METHOD OF SCREENING CANDIDATE COMPOUNDS FOR SUSCEPTIBILITY TO OXIDATIVE METABOLISM

TECHNICAL FIELD

The present invention relates to a method of screening compounds which are candidates for use as therapeutic agents for susceptibility to metabolic enzyme activity. More particularly, the present invention relates to a method of screening such candidate compounds for susceptibility to cytochrome P450-mediated metabolism.

| Table of Abbreviations | |
|---|---|
| ANOVA | analysis of variance |
| Cl$_{in}$ | intrinsic clearance |
| CYP | cytochrome P450 |
| CYP1A2 | cytochrome P450 1A2 reductase |
| CYP2C9 | cytochrome P450 2C9 reductase |
| CYP2C19 | cytochrome P450 2C19 reductase |
| CYP2D6 | cytochrome P450 2D6 reductase |
| CYP3A4 | cytochrome P450 3A4 reductase |
| CYP3A4OR | cytochrome P450 3A4 and human cytochrome P450 reductase |
| DCFH-DA | 2',7'-dichlorodihydrofluorescin diacetate |
| DCF | 2',7'-dicholorofluorescein |
| EDTA | ethylenediamine tetraacetate |
| 11α-OH progesterone | 11α-hydroxy progesterone |
| HP | Hewlett Packard |
| HPLC | high performance liquid chromatography |
| K$_m$ | Michaelis-Menten constant for enzyme-substrate reaction |
| λ em | maximal emission wavelength |
| λ ex | maximal excitation wavelength |
| mg pr. | milligrams protein |
| min | minute |
| NADPH | nicotinamide adenine dinucleotide phosphate (reduced) |
| ROS | reactive oxygen species |
| 6β-OH testosterone | 6β-hydroxy testosterone |
| SD | standard deviation |
| TAO | troleadomycin |
| UV | ultraviolet |
| V$_{max}$ | maximum velocity of enzyme-catalyzed reaction |

BACKGROUND ART

The advent of combinatorial chemistry techniques has enabled the identification of extremely high numbers of compounds that have potential as therapeutic agents. However, assays for drug metabolism that can rapidly identify those candidate compounds which have a lower potential for rapid metabolic degradation (i.e. short biological half-life) or drug-drug interaction have lagged behind the pace of synthesis and screening of pharmalogical activities. Thus, there is a long-felt need for high throughput assays to assess susceptibility of candidate compounds to metabolic degradation, particularly oxidative metabolism, that can rapidly identify suitable candidate compounds (i.e. metabolically stable) for further testing as therapeutic agents.

Of particular interest is the cytochrome P450 (CYP) superfamily of enzymes. The CYP enzymes catalyze reactions which have profound effects on the biological activities of drugs, environmental chemicals and endogenous compounds (Guengerich, *FASEB J* 6:667–668 (1992); Eastabrook, *FASEB J* 10:202–204 (1996); and Rendic and Di Carlo, *Drug Metab. Rev.* 29:413–580 (1997)). In recent years, advances in the study of CYP's by enzyme purification and characterization, gene cloning, and heterologous expression have indicated that five CYP isoforms, CYP1A2, CYP2C9, CYP2C19, CYP2D6, and CYP3A4, appear to be most commonly responsible for the metabolism of drugs in humans (Spatnegger and Jaeger, *Drug Metab. Rev.* 27:397–417 (1995)). Moreover, a number of CYP superfamily enzymes have been successfully expressed in bacterial, yeast, insect and mammalian cells, and have been used to identify substrates and/or inhibitors of these major CYP enzymes (Guengerich and Shimada, *Chem. Res. Toxicol.* 4:391–407 (1991); Birkett et al., *Trends Pharmacol. Sci.* 14:151–185 (1993); and Wrighton et al., *Drug Metab. Rev.* 25:453–484 (1993)).

To date, CYP metabolic activity, and/or inhibition thereof, has been assessed in most cases by performing in vitro incubation using cDNA-expressed enzymes or human liver microsomes (Parkinson, *Toxicol. Pathol.* 24:45–57 (1996)). Such assessments have required the development and use of assays for quantitative analysis of the parent drug molecules, or the metabolites thereof, which is time-consuming, labor-intensive and costly.

A journal article by Crespi et al. entitled "Microtiter Plate Assays for Inhibition for Human, Drug-metabolizing Cytochrome P450", *Anal. Biochem.* 248:188–190 (1997) describes a CYP inhibitor assay which utilizes microtiter plate-based fluorometric methods for several major xenobiotic-metabolising CYP isoenzymes, such as CYP3A4 and CYP1A2. Similar assays are also described in Kennedy and Jones, *Anal. Biochem.* 222:217–223 (1994) and in Donato et al., *Anal. Biochem.* 213:29–33 (1993). These assays utilize a known substrate for each of the major CYP isoenzymes as a model substrate. The ability of potential drug candidates to interact with CYP enzymes is ranked based on the relative inhibitory effect on metabolism of the model substrates. These assays are relatively fast as compared to other known methods, such as HPLC. However, these assays suffer from significant limitations in that they cannot directly assess the metabolic stability of candidate compounds.

In summary, prior art assays for susceptibility to oxidative metabolism, particularly CYP-mediated metabolism, rely on the measurement of the substrate and/or metabolite(s) in a reaction mixture. Such assays measure the presence of substrate and/or metabolite as a function of time and are thus limited to screening of one compound (or a best a few compounds) at a time. Therefore, what is needed is a rapid, high throughput assay which enables the screening of many compounds for susceptibility to oxidative metabolism in a single effort.

SUMMARY OF THE INVENTION

A method of screening a candidate compound for susceptibility to metabolism by a selected enzyme is disclosed herein. The method comprises the steps of reacting the candidate compound, an indicator compound precursor and the selected enzyme, the enzyme characterized as having a side reaction associated with metabolic activity of the enzyme wherein a chemical species capable of reacting with the indicator compound precursor is produced; and detecting as well as measuring an indicator compound, the indicator compound produced from the indicator compound precursor by reaction with the chemical species generated from the side reaction associated with metabolic activity of the enzyme, the presence of the indicator compound indicating the susceptibility of the candidate compound to metabolism by the enzyme.

Accordingly, it is an object of the present invention to provide a high throughput method of screening of candidate compounds for susceptibility to oxidative metabolism.

It is a further object of the present invention to provide a method of screening candidate compounds for susceptibility to oxidative metabolism which does not rely on the measurement or detection of the candidate compounds or their metabolites.

It is yet a further object of the present invention to provide a method of screening candidate compounds for susceptibility to oxidative metabolism which facilitates the screening of many candidate compounds in a single effort.

It is still a further object of the present invention to provide a method of screening candidate compounds for susceptibility to oxidative metabolism that is particularly suited to screening for susceptibility to cytochrome P450-mediated metabolism.

Some of the objects of the invention having been stated herein above, other objects will become evident as the description proceeds, when taken in connection with the accompanying Laboratory Examples and drawings as best described herein below.

DETAILED DESCRIPTION OF THE INVENTION

In accordance with the present invention, a method is provided for the screening of a candidate compound or substrate for susceptibility to metabolism by a selected enzyme. The method comprises the steps of reacting the candidate compound, an indicator compound precursor and the selected enzyme; and detecting the presence of an indicator compound. The indicator compound is produced from the indicator compound precursor by reaction with a chemical species that is produced from a secondary or side reaction associated with metabolic activity of the enzyme. The presence of the indicator compound indicates the susceptibility of the candidate compound to metabolism by the enzyme.

While the following terms are believed to be well understood by one of skill in the art, the following definitions are set forth to facilitate explanation of the invention.

The term "candidate compound" or "candidate substrate" is meant to refer to any compound wherein the characterization of the compound's susceptibility to enzymatic metabolism is desirable. Exemplary candidate compounds or substrates include xenobiotics such as drugs and other therapeutic agents, carcinogens and environmental pollutants, as well as endobiotics such as steroids, fatty acids and prostaglandins.

The term "selected enzyme" is meant to refer to an enzyme characterized as having a primary metabolic activity and as having a secondary or a side reaction associated with the primary metabolic activity of the enzyme. The side reaction produces a chemical species or a chemical byproduct that reacts with an indicator compound precursor in accordance with the method of the present invention. As described in the Laboratory Examples presented below, the reaction rates of the primary and side reactions are proportional to each other to facilitate qualitative and quantitative analysis of the susceptibility of the candidate compound or substrate to oxidative metabolism. Stated differently, the reaction rates of the primary and side reactions are related via a ratio that is analogous to the ratios commonly observed between gears in the mechanical arts.

A preferred example of a selected enzyme comprises a CYP. An additional example of a selected enzyme comprises xanthine oxidase. Other examples would be apparent to one of skill in the art, given the disclosure of the method of the present invention presented herein.

The terms "cytochrome P450" and "CYP" are meant to refer to a large family (often called a "superfamily") of hemoprotein enzymes capable of metabolizing xenobiotics such as drugs, carcinogens and environmental pollutants, as well as endobiotics such as steroids, fatty acids and prostaglandins. As used herein, these terms are meant to encompass all members of the CYP superfamily, regardless of species of origin. Thus, these terms are meant to refer to CYP superfamily members of microbial, invertebrate and vertebrate origin. It is preferred that these terms refer to CYP's of warm-blooded vertebrate species, including birds and mammals. Preferred sources of CYP's thus include bovine, porcine, ovine, canine, feline, equine, murine and avian sources. It is most preferred that these terms refer to CYP's of human origin.

All isoenzymes, or isoforms, within the CYP superfamily are contemplated to fall within the terms "cytochrome P450" and "CYP" as used herein. Particularly contemplated CYP isoforms include, but are not limited to, CYP1A2, CYP2C9, CYP2C19, CYP2D6, and CYP3A4, as these isoforms have been identified as those most commonly responsible for the metabolism of drugs in humans. Additional CYP superfamily members are described in U.S. Pat. Nos. 5,786,191 and 5,478,723, the contents of each of which are herein incorporated by reference.

The terms "chemical species" and "chemical byproduct" are meant to refer to a species or byproduct that is formed from a side or secondary reaction associated with the primary metabolic activity of a selected enzyme. The terms "chemical species" and "chemical byproduct" are further characterized in that the species or byproduct produced from the secondary or side reaction associated with the metabolic activity of the enzyme is capable of reacting with an indicator compound precursor in accordance with the methods of the present invention.

Exemplary chemical species comprise the "reactive oxygen species" or "ROS" produced from side reactions of several enzymes, including CYP-superfamily enzymes and xanthine oxidase. Exemplary ROS comprise superoxide anion ±, hydrogen peroxide ($H_2O_2$) and hydroxyl radical (OH·).

The term "indicator compound precursor" is meant to refer to a chemical compound that reacts with the chemical species produced from the side reaction associated with metabolic activity of the enzyme. The term "indicator compound" is meant to refer to the compound produced by the reaction of the indicator compound precursor and the chemical species. As noted above, the presence of the indicator compound indicates the susceptibility of the candidate compound to metabolism by the selected enzyme. The preferred indicator compound is readily detectable using a standard detection technique, such as fluorescence or chemiluminescence spectrophotometry, colorimetry, and the like.

Exemplary indicator compound precursors thus include, but are not limited to, compounds which are converted to fluorogenic/fluorescent compounds, chemiluminescent compounds, colorimetric indicator compounds, and combinations thereof. A particularly contemplated indicator compound precursor/indicator compound system comprises the fluorogenic probe 2',7'-dichlorodihydrofluorescin-diacetate (DCFH-DA) and its fluorescent counterpart, 2',7'-dichlorofluroescein (DCF), as described in the Examples below. Another indicator compound precursor/indicator compound system comprises epinephrine and adrenochrome. This indicator is detected by colorimetric methods. This system has been used to demonstrate formation of oxygen radicals (Knobeloch et al., *J. Appl. Toxicol.* 10:1–5 (1990)). However, applicants have observed that this system is not preferred for use with CYP3A4-mediated reactions.

Following long-standing patent law convention, the terms "a" and "an" mean "one or more" when used in this application, including the claims.

It is contemplated that the method of the present invention may be performed within standard multi-well assay plates as are well known in the art, such as the 96-well micro-titer plates that are available from ICN Flow. Thus, a plurality of candidate compounds can be simultaneously screened for susceptibility to metabolism by a selected enzyme within multiple wells of a multi-well plate.

As would be apparent to one of skill in the art from the disclosure of the present invention, it is also contemplated that the methods of the present invention may be performed in a cell-free reaction and/or in a cell-based, in vitro reaction. Exemplary cell-based, in vitro platforms suitable for modification in accordance with the method of the present invention are described in Parkinson, *Toxicol. Pathol.* 24:45–57 (1996). As would also be apparent to one of skill in the art from the disclosure of the present invention, the methods of the present invention are contemplated to be useful for other combinations of indicator compound precursor-indicator compound. For example, Ferric-EDTA is contemplated to be an indicator compound precursor which can give rise to a chemiluminescent product in the presence of a reactive oxygen species (Puntarulo and Cederbaum, *Arch. Biochem. Biophys.* 258: 510–518 (1987)).

The following Laboratory Examples have been included to illustrate preferred modes of the invention. Certain aspects of the following Laboratory Examples are described in terms of techniques and procedures found or contemplated by the present inventors to work well in the practice of the invention. These Laboratory Examples are exemplified through the use of standard laboratory practices of the inventors. In light of the present disclosure and the general level of skill in the art, those of skill will appreciate that the following Laboratory Examples are intended to be exemplary only and that numerous changes, modifications and alterations can be employed without departing from the spirit and scope of the invention.

Laboratory Examples

Materials Used in the Examples

CYP3A4OR was a gift from Glaxo Wellcome Inc. (Research Triangle Park, N.C.). CYP1A2 SUPERSOME™ and furafylline were purchased from Gentest Corp. (Woburn, Mass.). Testosterone, 6β-hydroxytestosterone and 11α-hydroxyprogesterone were obtained from Steraloids, Inc. (Wilton, N.H.). Dextromethorphan was kindly provided by Dr. Scott Smith (GLP Laboratory, School of Pharmacy at University of North Carolina at Chapel Hill). Ethoxyresorufin, 7-benzyloxyresorufin, resorufin, and 2',7'-dichlorodihydrofluorescin diacetate (DCFH-DA) were obtained from Molecular Probes, Inc. (Eugene, Oreg.). 2',7'-dichlorofluorescein (DCF)was obtained from Aldrich Chemical Co. (Milwaukee, Wis.). Ketoconazole, TAO, acetophenatidin (N-[4-ethoxyphenyl]acetamide; phenacetin), N-acetyl-p-aminophenol (acetaminophen), pluronic F-68, and NADPH were obtained from Sigma Chemical Co. (St. Louis, Mo.). All the other chemicals and reagents were the highest grade available from commercial sources.

Comparison—Prior Art Methods for Analysis of Metabolites of Testosterone, Phenacetin, Ethoxyresorufin and Benzyloxresorufin (which are also assayed below in the Examples)

An HPLC method (Lee et al., *Arch. Biochem. Biophy.* 319:157–167 (1995)) after the below-described modification was used for analysis of testosterone. Briefly, methylene chloride (2 ml) and internal standard (10 µl of 1 mg/ml)

11α-OH progesterone were added to an incubation mixture (0.5 ml), and the resultant solution was mixed and centrifuged at 10,000 g for 5 min. The organic layer was removed and evaporated under a nitrogen stream. The residue was reconstituted with 0.5 ml mobile phase (40% $CH_3CN$ and 60% $H_2O$). Chromatographic separation was achieved using a Hewlett Packard (HP) 1100 series HPLC system with a sphereclone 5 μm C6 column (250×4.5 mm; Phenomenex, Torrence, Calif.). Testosterone, 6β-OH testosterone and 11α-OH progesterone were eluted under isocratic conditions and were monitored by UV absorption at 230 nm. The retention times for the testosterone, 6β-OH testosterone and 11α-OH progesterone were 15.78, 4.81, and 10.70 min, respectively.

As described above with respect to testosterone, chromatographic separation of phenacetine, its potential metabolites including acetaminophen, and other interfering components was accomplished using a HP1100 series HPLC system. Briefly, acetonitrile (0.4 ml) was added to a reaction mixture (0.5 ml) of phenacetin as described previously. The resultant solution was mixed and centrifuged (15,000×3 min). An aliquot (100 μl) of the supernatant was injected to an Advantage100 5 micron C18 column (4.6×250 mm, Thomas Liquid Chromatography). The mobile phase comprised $CH_3CN$ and $H_2O$ with a gradient from 1 to 99% $CH_3CN$ over 20 min at a flow rate of 1 ml/min. Phenacetin and its potential metabolites were monitored at 244 nm.

Resorufin, a common metabolite of ethoxyresorufin by CYP1A2 and of benzyloxyresorufin by CYP3A4, was measured by fluorescence spectrophotometry as described above for DCF, with excitation and emission wavelength at 570 and 583 nm, respectively.

Summary of Results from the Examples

Figure 4:
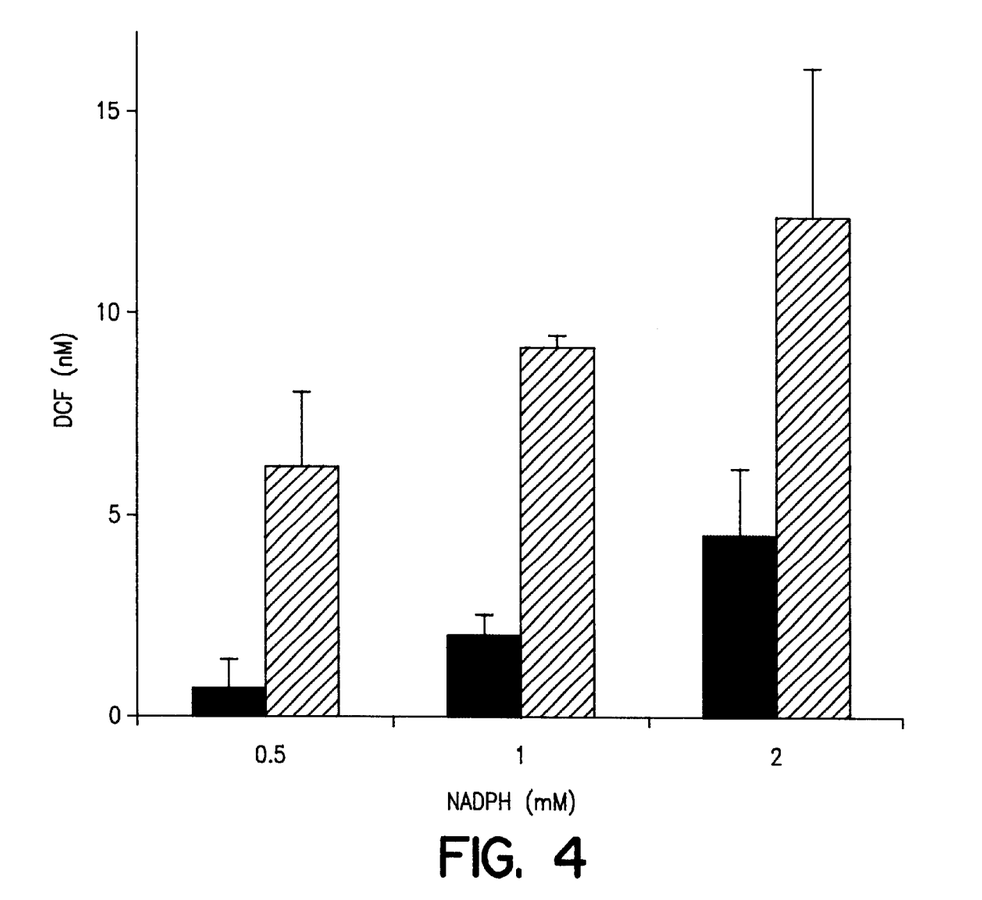
FIG. 4 is a bar graph depicting the effect of NADPH concentrations on DCF formation at 20 min (solid bars) and at 30 min (hatched bars) during CYP3A4-mediated testosterone oxidation. Incubation conditions are described later herein.

Indicator compound formation was in proportion to the formation of the corresponding metabolites in CYP3A4- (FIGS. 2 and 5) or CYP1A2-mediated (FIG. 8a) oxidation of substrates tested. Formation of the indicator compound, DCF, was dependent on the presence of and concentration of NADPH (FIG. 4). This indicates that formation of DCF is dependent on CYP-mediated metabolism of a substrate because CYP-mediated metabolism is dependent on adequate concentration of NADPH. Furthermore, formation (velocity) of 6β-OH testosterone (the metabolic product of testosterone) and DCF (the indicator compound) increased with increasing testosterone concentration and ultimately reached a plateau at high substrate concentration (FIG. 5) as would be expected for an enzyme-catalyzed reaction. A similar observation was made for DCF formation during the CYP1A2-mediated metabolism of ethoxyresorufin (FIG. 9).

Figure 10:
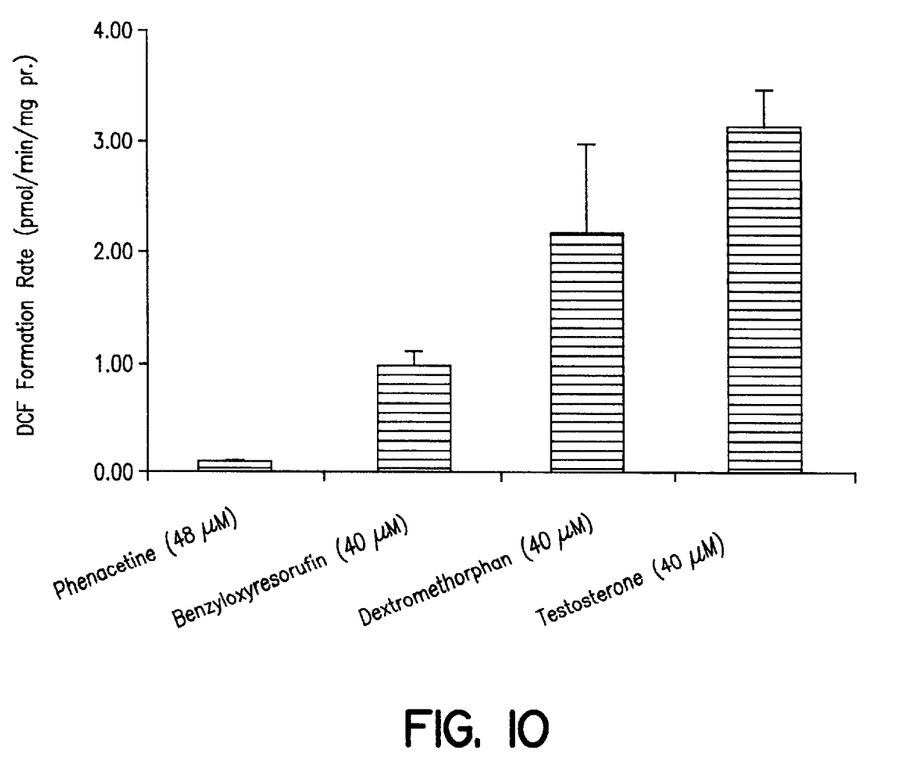
FIG. 10 is a bar graph depicting the comparison of DCF formation rate for CYP3A4-mediated metabolism of phenacetin, benzyloxyresorufin, dextromethorphan and testosterone under the incubation conditions described later herein.

Furthermore, the formation of DCF during CYP3A4-mediated metabolism of testosterone and CYP1A2-mediated metabolism of ethoxyresorufin was inhibited by CYP3A4-specific inhibitors ketoconazole and TAO (FIG. 6), and CYP1A2-specific inhibitor furafulline (FIG. 8), respectively. Finally the results in FIG. 10 show that formation of the indicator compound (velocity) is very low when metabolism of phenacetine (not a CYP3A4-substrate) is attempted by CYP3A4, and quite high (>10 to 20-fold higher) when dextromethorphan or testosterone (both are good substrates of CYP3A4) are metabolized by CYP3A4 (FIG. 10). In summary, these results demonstrate that the indicator compound (DCF) formation occurs only when CYP3A4 or CYP1A2 metabolize their respective substrates effectively, that the rate of formation of DCF during these CYP3A4- and CYP1A2-mediated metabolism reflects the rate at which these enzymes metabolize their respective substrates, and that inhibition of these enzyme-mediated metabolism also results in reduction in the formation of DCF.

EXAMPLE 1

Screen for Susceptibility to Metabolism by CYP Isoenzyme CYP3A4 Using a Fluorescent Indicator Compound This Example pertains to a high throughput assay that assesses the metabolic stability of potential drug molecules toward CYP-mediated oxidation without requiring analysis of either the drug molecules or their metabolites.

Figure 1:
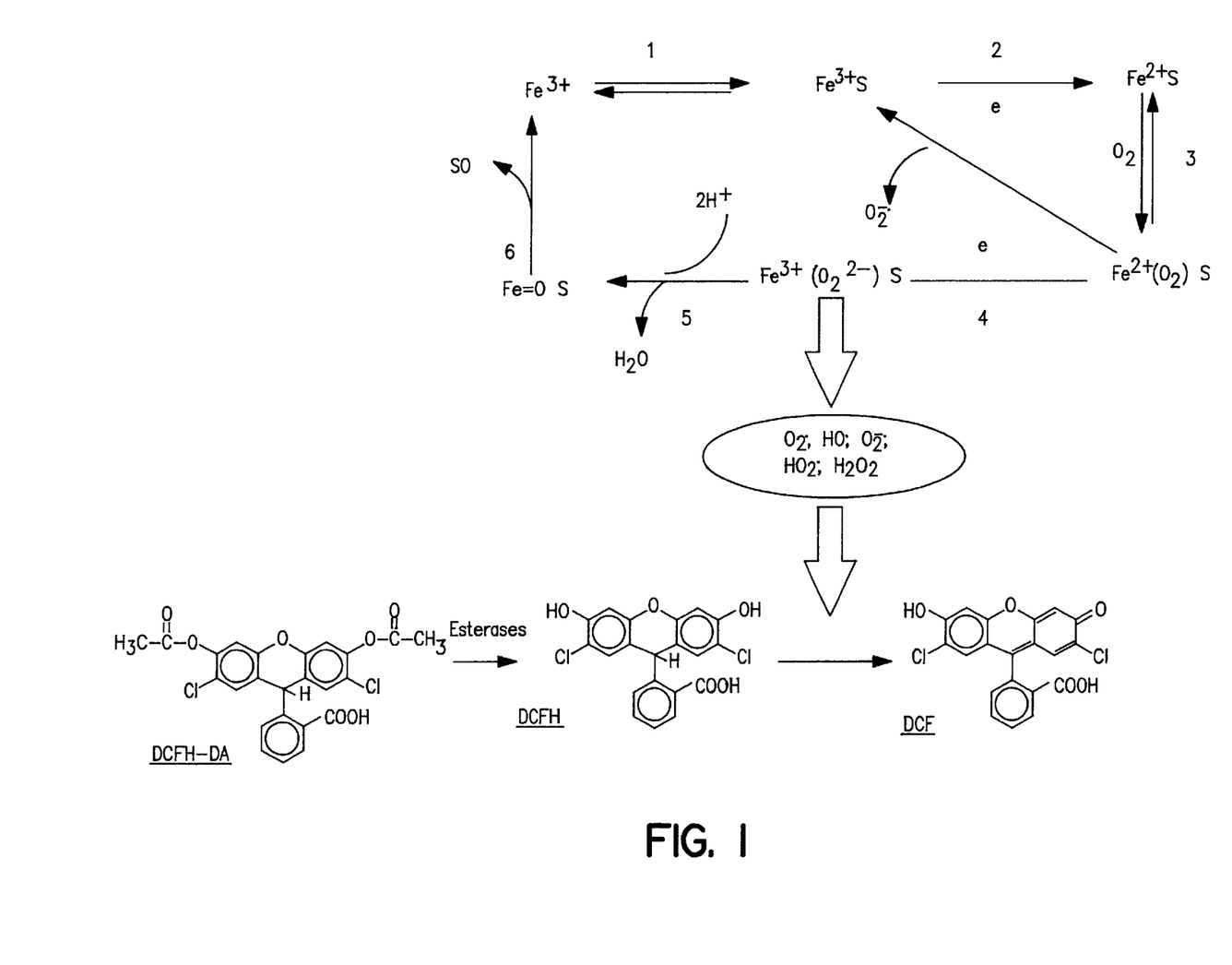
FIG. 1 is a schematic of the secondary or side reaction associated with cytochrome P450 metabolism which produces reactive oxygen species, along with a schematic of the reaction between the reactive oxygen species and the indicator compound precursor in accordance with the method of the present invention.

Cytochrome P450 (CYP) enzymes have been shown to be one of the main producers of reactive oxygen species (ROS) in the liver cell. Superoxide anion ±, hydrogen peroxide ($H_2O_2$), and hydroxyl radical (OH˙) can be formed in CYP-catalyzed reactions (Bernhardt, *Rev. Physiol. Biochem. Pharmacol.* 127:138–221 (1995))(FIG. 1). It has also been demonstrated that during NADPH oxidation in microsomes, $H_2O$ was generated (Gillette et al., *J. Pharmacol. Exp. Ther.* 119:532–540 (1957)). "Uncoupling" of CYP-dependent reactions was described for different drugs and chemicals such as n-hexane (Staudt et al., *Eur. J. Biochem.* 46:99–106 (1974)), hexobarbital, benzphetamine (Hildebrandt and Roots, *Arch. Biochem. Biophy.* 171:385–397 (1975)). Despite this recognition that the production of ROS is common to almost all CYP isoenzyme-mediated oxidations, the development of a CYP-mediated metabolism assay that does not require measurement of the individual drug molecules or their metabolites, but that measures signals generated by utilizing ROS has not been suggested. Such an assay is particularly described in this Example.

A fluorogenic probe 2',7'-dichlorodihydrofluorescin-diacetate (DCFH-DA) was added to a CYP-mediated reaction mixture containing a substrate, isoenzyme, and NADPH in Tris buffer (50 mM, pH 7.4). The substrate comprised testosterone. Metabolism of the substrate was examined by measurement of formation of the resulting metabolite (prior art method) and/or 2',7'-dichlorofluroescein (DCF; method in accordance with the present invention) which was converted from the DCFH-DA in the presence of the ROS produced by CYP-mediated reactions. Dextromethorphan and benzyloxyresorufin served as two additional substrates, and phenacetine (not a CYP3A4 substrate) as a negative control for CYP3A4 to test whether the method of the present invention could differentiate substrates with different metabolic rates or substrates from non-substrates.

DCF Formation During CYP3A4-mediated Metabolism of Testosterone—Initial studies were conducted to examine whether DCF was formed during CYP-mediated oxidation using testosterone hydroxylation by CYP3A4OR. A reaction mixture (total 2 ml) comprising DCFH-DA (5.36 μM), CYP3A4OR (0.5 mg/ml) and testosterone (50 μM) in Tris buffer (50 mM, pH 7.4) was prepared. The reaction was initiated by adding NADPH (0.5 mM) and allowed to proceed at room temperature. The fluorescent spectra (emission and excitation) of DCF formed from the incubation was determined using LS50B Luminescence Spectrometer (Perkin-Elmer, Norwalk, Conn.). The spectra were compared with that of standard DCF in Tris buffer (50 mM, pH 7.4). An incubation mixture that contained all the components as described previously except for DCFH-DA served as a control.

The excitation and emission spectra of the incubation mixture that contained testosterone, CYP3A4OR, NADPH and DCFH-DA were shown with maximal excitation and emission wavelength at 504 and 522 nm, respectively. As expected, the excitation and emission spectra of standard DCF matched those of the incubation mixture. Reactions that were devoid of DCFH-DA failed to show a measurable fluorescent signal, indicating that fluorescence observed upon CYP3A4-mediated testosterone metabolism was derived from DCFH-DA.

Specificity of DCF Formation to CYP3A4-mediated Testosterone Metabolism—After obtaining the maximal excitation and emission wavelengths of DCF under experimental conditions, the fluorescent signals at the maximal excitation and emission wavelengths were determined for incubation reactions that contained 12.5, 25, and 50 µM testosterone to test whether DCF formation was dependent on testosterone concentrations. The incubation conditions were the same as those described above. The formation of DCF at 10 min post addition of NADPH was calculated based on the standard curve of DCF. The standard curve covered DCF concentrations ranging from 0.05 to 50 nM. In parallel, DCF formation was determined with incubation reactions that were devoid of any of NADPH, CYP3A4 or testosterone.

This experiment was designed to test whether DCF formation during CYP3A4-mediated testosterone metabolism was specific to testosterone metabolic process. The results, presented in Table 1, demonstrated that hydroxylation of testosterone did not occur in the absence of NADPH or CYP3A4OR, as no 6β-OH testosterone was observed by the HPLC method. Likewise, a negligible fluorescent signal was detected from these samples (70±11 and 29±1 for samples without NADPH and CYP3A4OR, respectively). A relatively weak fluorescent signal was observed in the absence of testosterone (Table 1); this may reflect CYP-mediated metabolism of some of the components of the incubation medium (e.g. lipids, $CH_3OH$).

Figure 2:
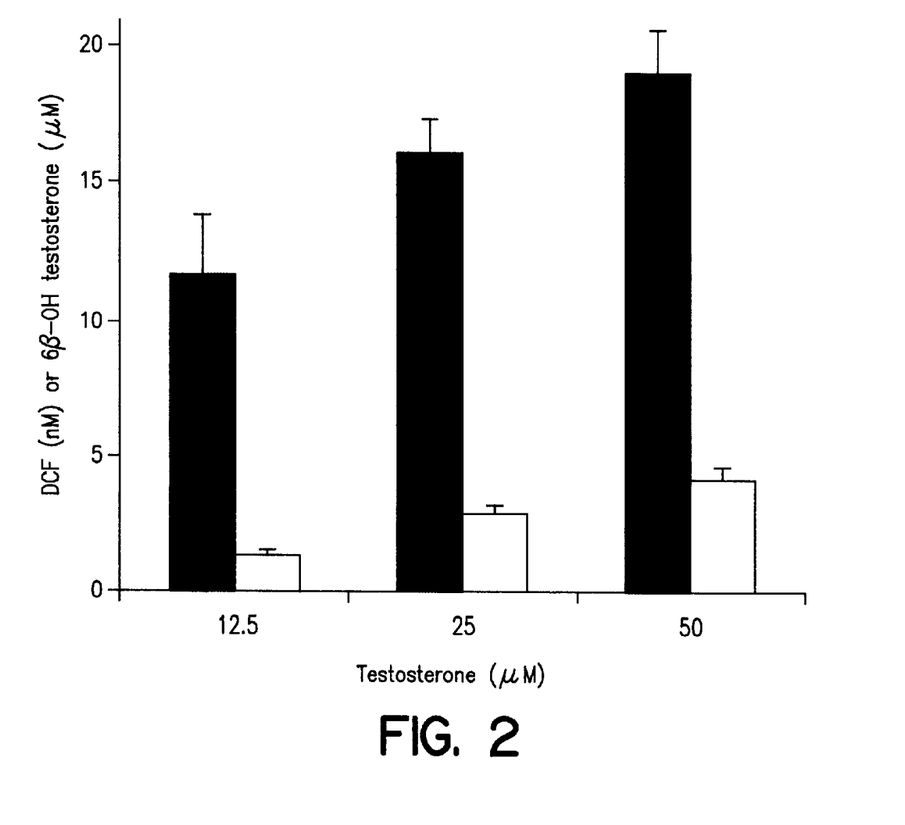
FIG. 2 is a bar graph depicting formation of DCF (solid bars) and 6β-OH testosterone (open bars) upon incubation of testosterone with CYP3A4OR in the presence of NADPH and DCFH-DA. Detailed experimental conditions are described in Example 1.

Consistent with the fact that formation of 6β-OH testosterone increased from 0.410±0.060 to 1.261±0.170 µg/ml as testosterone concentration increased from 12.5 to 50 µM, fluorescent intensity also increased from 363±38 to 505±29. DCF formation from the reaction was calculated based on the net fluorescent signal, which was the difference between the fluorescent intensity of incubation samples containing testosterone and those without testosterone but with the same volume of $CH_3OH$, which was used as solvent for testosterone. The relationship between testosterone concentration and formation of DCF or 6β-OH testosterone is presented in FIG. 2. FIG. 2 demonstrates that DCF formation reflected CYP3A4-mediated oxidation of testosterone to 6β-OH testosterone.

TABLE 1

DCF and 6β-OH testosterone formation during CYP3A4-mediated testosterone metabolism (n = 3)[a]

| Experimental Conditions | Fluorescence Intensity at λ ex 503 and λ em 522 nm | 6β-OH testosterone (µg/ml) |
| --- | --- | --- |
| Without NADPH | 70 ± 11 | ND[b] |
| Without CYP3A4OR | 29 ± 1 | ND[b] |
| Without testosterone | 139 ± 3[c] | ND[b] |
| Testosterone (12.5 µM) | 363 ± 38[d] | 0.41 ± 0.06 |
| Testosterone (25.0 µM) | 449 ± 21[d] | 0.87 ± 0.11 |
| Testosterone (50.0 µM) | 505 ± 29[d] | 1.26 ± 0.17 |

[a]Data were presented as mean ± SD
[b]6β-OH testosterone was not detected by HPLC method as described above.
[c]Significantly higher as compared to that in the absence of NADPH or CYP3A4OR (p < 0.05)
[d]Significantly higher as compared to that in the absence of testosterone (p < 0.05)

Effect of DCFH-DA and NADPH Concentrations on DCF Formation Specific to CYP3A4-mediated Testosterone Metabolism—DCFH-DA (1, 2.5 or 5 µM) was incubated with CYP3A4OR (0.5 mg/ml protein), testosterone (33 µM), and NADPH (1 mM) in Tris buffer. DCF concentration was measured at 5, 10, 20 and 30 min. The effect of NADPH concentration on DCF formation at 20 and 30 min was examined with incubations containing NADPH (0.5, 1 or 2 mM), testosterone (33 µM), and DCFH-DA (2.5 µM).

Figure 3:
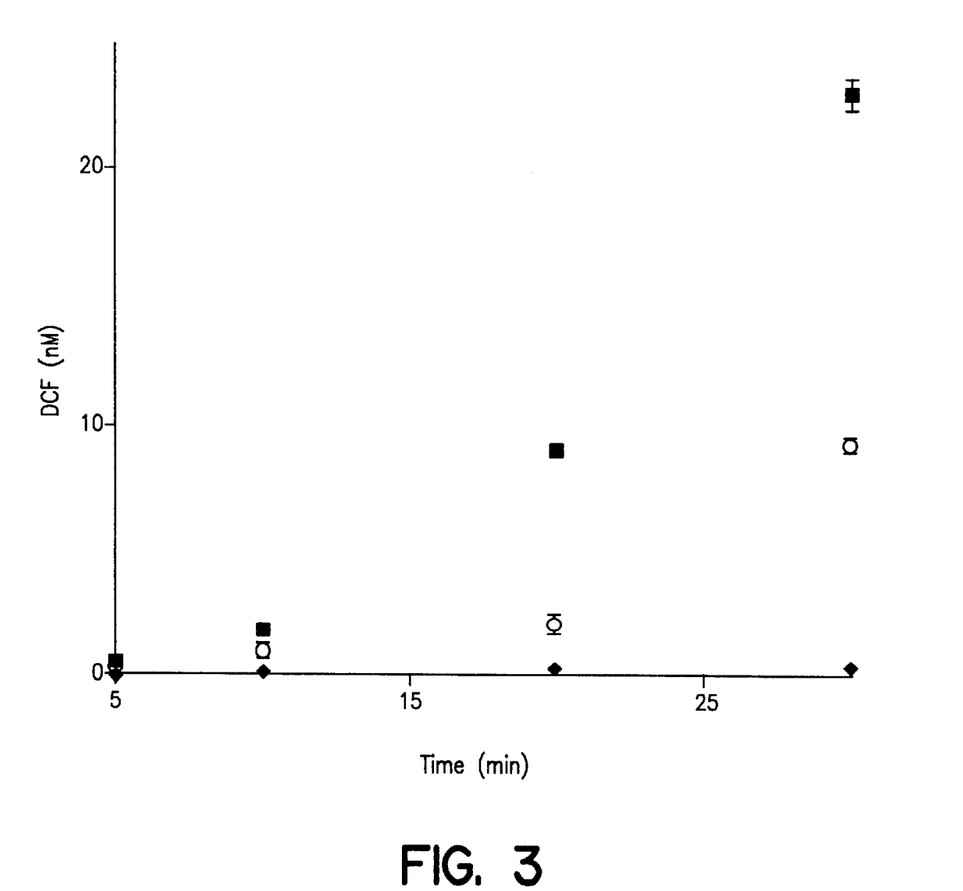
FIG. 3 is a point graph depicting effect of DCFH-DA concentrations (diamonds, circles and squares represent 1, 2.5, and 5 μM DCFH-DA, respectively) on DCF formation as a function of time during CYP3A4-mediated testosterone oxidation. Incubation conditions are described later herein.

FIG. 3 shows the effect of DCFH-DA concentration on DCF formation. In a reaction system with a fixed concentration of substrate (33 µM testosterone), enzyme (0.5 mg/ml CYP3A4OR), and cofactor (1 mM NADPH), formation of DCF depended on DCFH-DA concentrations. DCF formation increased with an increase in DCFH-DA concentrations. DCF formation was linear for up to 20 min with DCFH-DA concentration at 1.25 or 2.5 µM.

There was a trend that DCF formation increased as NADPH concentration increased, as shown in FIG. 4. For example, DCF formation in 10 min was 0.68±0.75 nM from incubation with 0.5 mM NADPH and increased to 4.56±1.63 nM with 2 mM NADPH. Indeed, as also shown in FIG. 4, a significant difference in DCF formation in 20 and 30 min was observed among incubation samples that contained different NADPH concentrations (0.5, 1 and 2 mM).

Metabolism Kinetics Parameters for Testosterone Hydroxylation by CYP3A4—DCFH-DA (2.5 µM) was incubated with testosterone (5–40 µM), CYP3A4OR (0.5 mg/ml protein) and NADPH (1 mM) in Tris buffer. The total incubation volume was 1 ml. The formation of DCF was measured at 10 and 20 min post addition of NADPH. Triplicate incubations were performed at each concentration. A Michaelis-Menten function was used to fit to DCF formation rate vs. testosterone concentration data to obtain estimates of the relevant kinetic parameters using the nonlinear least-squares regression method (Winnonlin Scientific Consulting Co., Apex, N.C.). Parallel experiments were conducted to obtain the kinetic parameters based on measurement of 6β-OH testosterone, a specific CYP3A4-mediated metabolite of testosterone, with the HPLC-UV method. The concentration range of testosterone used for the HPLC-UV method was 10 to 75 µM.

Figure 5A:
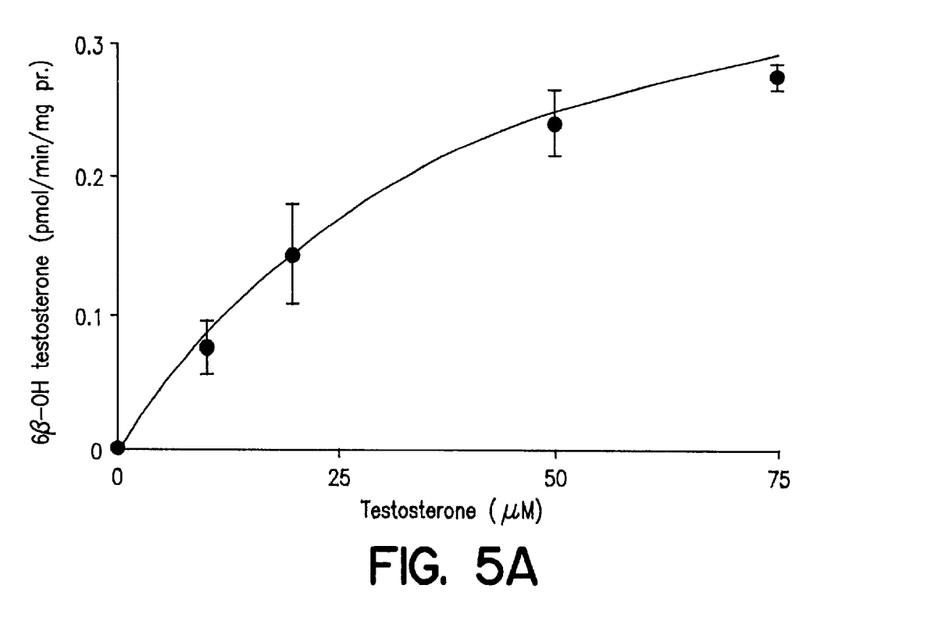
FIG. 5 presents two line graphs which depict the relationship between testosterone concentrations and velocity of (a) 6β-OH testosterone or (b) DCF formation. Incubation conditions are described later herein.

This experiment was conducted to determine if saturable kinetics observed during CYP3A4-catalyzed oxidation of testosterone (i.e. a plateau reached for the velocity of 6β-OH testosterone formation at high concentrations of testosterone, FIG. 5a, is also observed when DCF formation is used to monitor the same reaction. It is clear from FIG. 5 that indeed the kinetics of testosterone metabolism by CYP3A4 appears similar when measured by 6β-OH testosterone formation or DCF formation.

The $K_m$, which is a kinetic parameter that defines the concentration of the substrate at which half-maximal velocity is reached, was determined by measurement of DCF formation (11.9 µM) and compared with that, determined by 6β-OH testosterone formation (43.4 µM). An approximately 3.5-fold lower value obtained with DCF measurement vs. 6β-OH testosterone measurement is significantly different, however it is still within the variability of $K_m$ measurement observed among different laboratories and when determined by different methods.

The $V_{max}$ value, the maximum velocity obtainable for a given concentration of enzyme and co-factors (i.e. NADPH), was not compared directly between the two methods. This comparison is made by determining the ratio of number of moles of DCF formed for each mole of 6β-OH testosterone formed. Establishment of such stoichiometric relationship between two reactions is accomplished by systematic study under a variety of reaction conditions. Such studies allow determination of $V_{max}$ as well as $K_m$ for CYP-mediated metabolism of substrates by measurement of fluorescence signal due to DCF formation.

Effect of Inhibitors of CYP3A4. Ketoconazole and TAO, on Testosterone-metabolism-mediated DCF Formation—Ketoconazole (1 µM) or TAO (10 µM) was incubated with testosterone (10 μM), CYP3A4OR (0.5 mg/ml), NADPH (1 mM), and DCFH-DA (2.5 μM). DCF formation at timed intervals (from 5 to 30 min) was compared between incubations in the presence and absence of ketoconazole or TAO.

Figure 6:
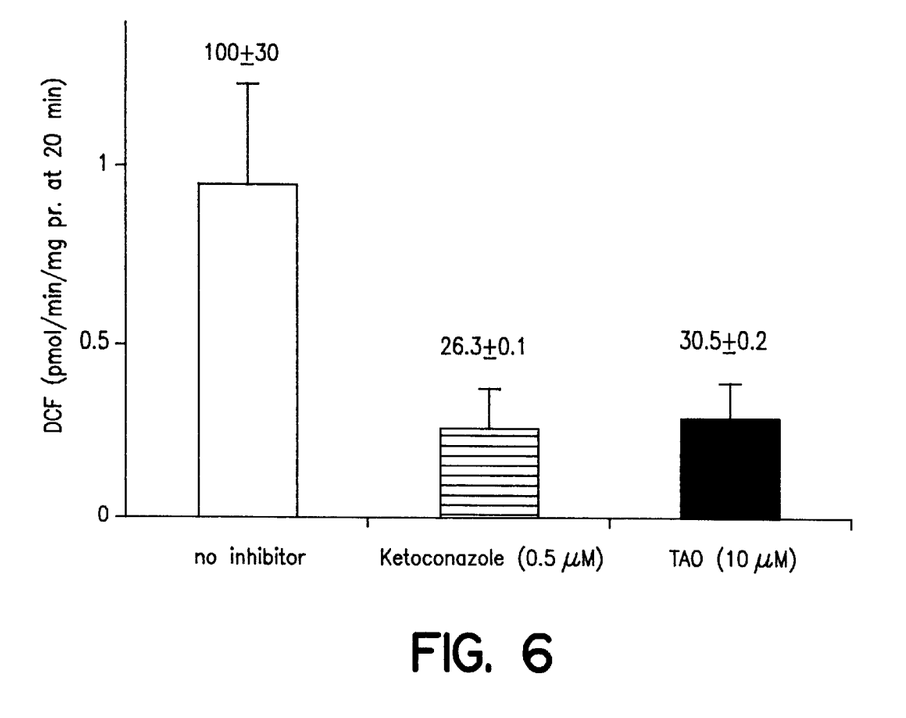
FIG. 6 presents a bar graph which depicts DCF formation rates during CYP3A4-mediated testosterone oxidation in the absence (open bars) and presence of ketoconazole (0.5 μM; hatched bars) or TAO (10 μM; solid bars). Other conditions are described later herein.

DCF formation was significantly lower in the presence of 0.5 μM ketoconazole or 10 μM TAO as compared to the control (two-way ANOVA, $p<0.05$). For example, DCF formation rate in the presence of 0.5 μM ketoconazole or 10 μM TAO was 26% and 30% of the control, respectively (FIG. 6). Both ketoconazole and TAO are known to be specific inhibitors of CYP3A4-mediated metabolism, and are expected to attenuate the metabolism of substrates by this enzyme. The fact that DCF formation is also attenuated by ketoconazole and TAO during CYP3A4-mediated oxidation of testosterone clearly demonstrates that DCF formation is truly representative of the CYP3A4-mediated metabolism of compounds. These results also show that DCF formation can be used to evaluate the inhibition of CYP3A4-mediated metabolism of substrates.

Determination of Kinetics of Dextromethorphan, Benzyloxyresorufin And Phenacetin Metabolism by CYP3A4— This experiment was conducted to examine whether measurement of DCF formation in CYP3A4-mediated reactions reflects the difference in metabolic kinetics of substrates as was observed with prior art methods. Dextromethorphan (2–100 μM), benzyloxyresorufin (5–100 μM), or phenacetin (48 μM) was incubated with CYP3A4OR (0.5 or 1 mg/ml), DCFH-DA (2.5 μM) and NADPH (1 mM) in Tris buffer. In the case of benzyloxyresorufin, pluronic F-68 (2%, 5 μl) was added to the reaction mixture (Crespi et al., *Anal. Biochem.* 248:188–190). DCF formation was measured at timed intervals.

Parallel experiments were conducted to measure formation of 3-methoxymorphinan (metabolite of dextromethorphan) and resorufin (metabolite of benzyloxymorphinan) by HPLC and fluorescence spectrophotometry, respectively, as described above. Potential metabolites of phenacetin were monitored by HPLC. The incubation conditions for benzyloxyresorufin and dextromethorphan were same as described above. Phenacetin (92 μM) was incubated with CYP3A4OR (0.5 or 1 mg/ml) and NADPH (1 mM) for 10 or 30 min. Incubation in the absence of NADPH was used as control.

Figure 7A:
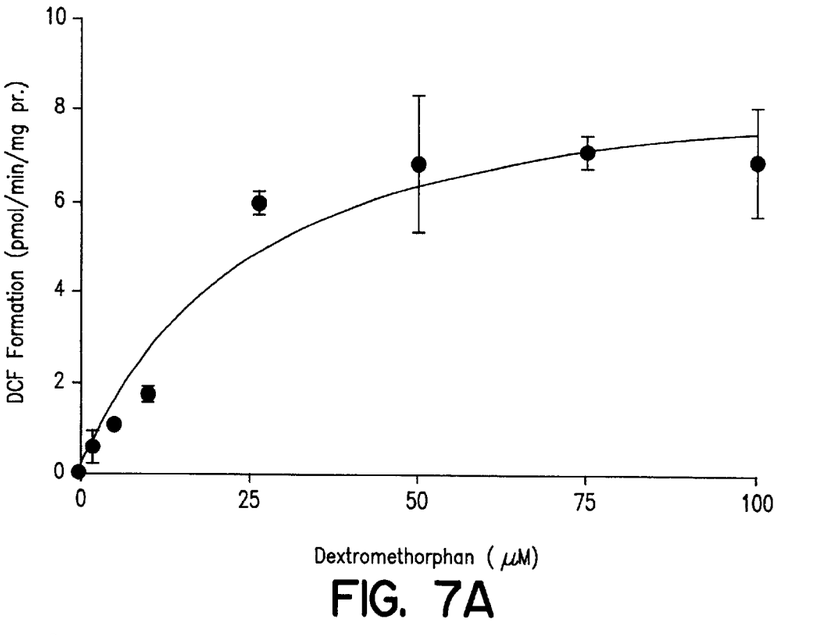
FIG. 7 presents two line graphs which depict the relationship between DCF formation rates and concentrations of (a) dextromethorphan or (b) benzyloxyresorufin. Experimental conditions are described later herein.
Figure 7B:
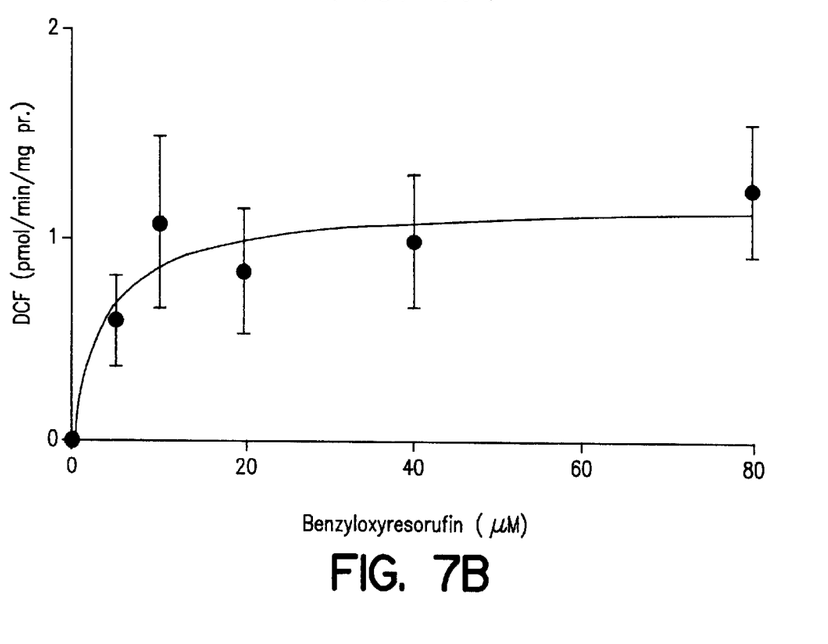

This experiment was also undertaken to test whether the method of the present invention could be applied to other drug molecules (e.g. dextromethorphan and benzyloxyresorufin) that are metabolized by CYP3A4 and to those (e.g. phenacetin) that are not, i.e. can the present method distinguish between compounds that are rapidly metabolized by CYP3A4 from a compound that is poorly metabolized by CYP3A4? As was observed above with testosterone, DCF formation was also dependent on concentration of dextromethorphan or benzyloxyresorufin, as shown in FIGS. 7a and 7b. However, testosterone and dextromethorphan exhibited significantly higher maximal velocity as compared to benzyloxyresorufin, as shown in Table 2. Further, the DCF formation rate from potential metabolism of phenacetin by CYP3A4 was almost negligible as compared to the other three substrates (FIG. 10). These observations are consistent with the previous results which indicate that phenacetin is not a substrate for CYP3A4. Thus, DCF formation can clearly identify a metabolically stable compound from those that exhibit different levels of metabolic instability toward CYP3A4.

TABLE 2

Comparison of apparent kinetic parameters $K_m$ and $V_{max}$ for CYP3A4-substrates and non-substrates by measurement of DCF formation

| Compound | Apparent $K_m$ (μM) | Apparent $V_{max}$ (pmol DCF/min/mg pr.) |
|---|---|---|
| Testosterone | 11.95 ± 3.58 | 6.83 ± 0.84 |
| Dextromethorphan | 24.2 ± 9.2 | 9.50 ± 1.20 |
| Benzyloxyresorufin | 3.79 ± 2.34 | 1.17 ± 0.14 |
| Phenacetin[a] | — | — |

[a]Phenacetin was not significantly metabolized by CYP3A4, and DCF formation was not sufficiently high to allow measurement.

EXAMPLE 2

Screen for Susceptibility to Metabolism by CYP Isoenzyme CYP1A2 Using a Fluorescent Indicator Compound Determination of kinetics of ethoxyresorufin metabolism by CYP1A2—Initial experiments were conducted to examine ethoxyresorufin concentration-dependent formation of DCF. Ethoxyresorufin (0.5, 5, 50 μM) was incubated with CYP1A2 SUPERSOME™ (sold under this trademark by Gentest Corp., Wobum, Mass.) (90 μg/ml protein), DCFH-DA (5 μM) and NADPH (1 mM). Formation of resorufin and DCF for the sample was measured at 8 and 10 min, respectively. The kinetic parameters then were obtained by incubating ethoxyresorufin (0.5–2.5 μM) with CYP1A2 SUPERSOME™ (90 μg/ml protein), DCFH-DA (5 μM), and NADPH (1 mM) for 5 min for measurement of resorufin formation and 15 min for measurement of DCF formation. Formation of DCF and resorufin was determined by fluorescence spectrophotometry. All experiments were performed in triplicate unless otherwise indicated.

The effect of furafylline, a specific inhibitor of CYP1A2, on CYP1A2-mediated ethoxyresorufin metabolism was also examined. Furafylline (1 and 10 μM) was pre-incubated with CYP1A2 SUPERSOME™ (180 μg/ml protein) and NADPH (4 mM) in Tris buffer in a total volume of 0.5 ml for 10 min. Then ethoxyresorufin (5 μM), DCFH-DA (5 μM), and supplemental NADPH was added to the mixture. The reaction proceeded for 5 min. Formation of DCF and resorufin in the presence of furafylline was compared with that of control that did not contain furafylline.

Figure 8A:
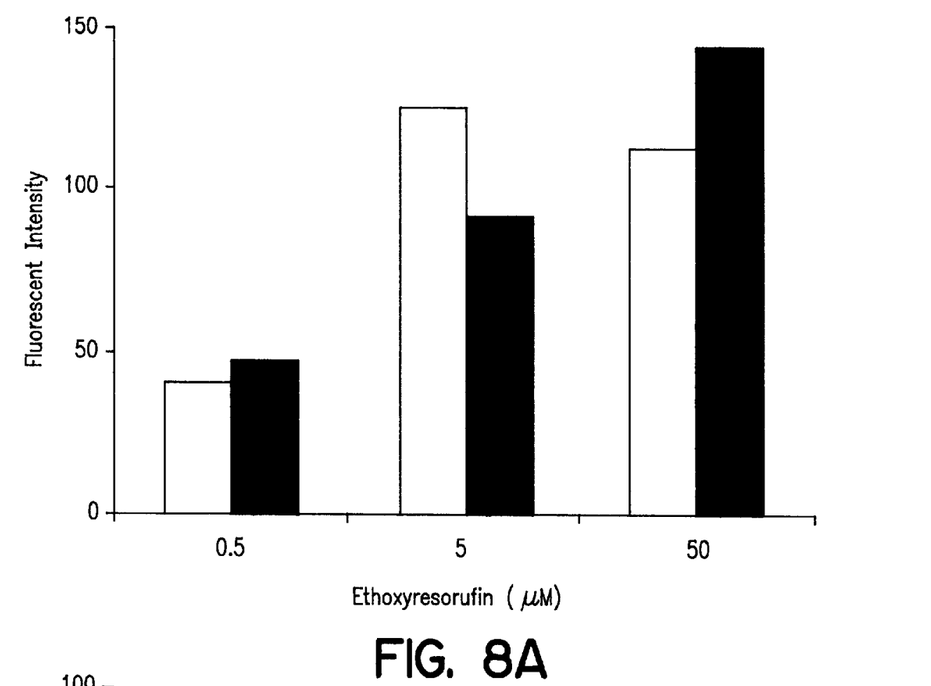
FIG. 8 presents two bar graphs which depict (a) concentration-dependent formation of DCF (λex 503 nm and λem 522 nm; open bars) and resorufin (λex 570 nm and λem 583 nm; solid bars) and (b) effect of furafylline on DCF (dotted bars) and resorufin (hatched bars) formation during CYP1A2-mediated metabolism of ethoxyresorufin. Other conditions are described later herein.
Figure 9A:
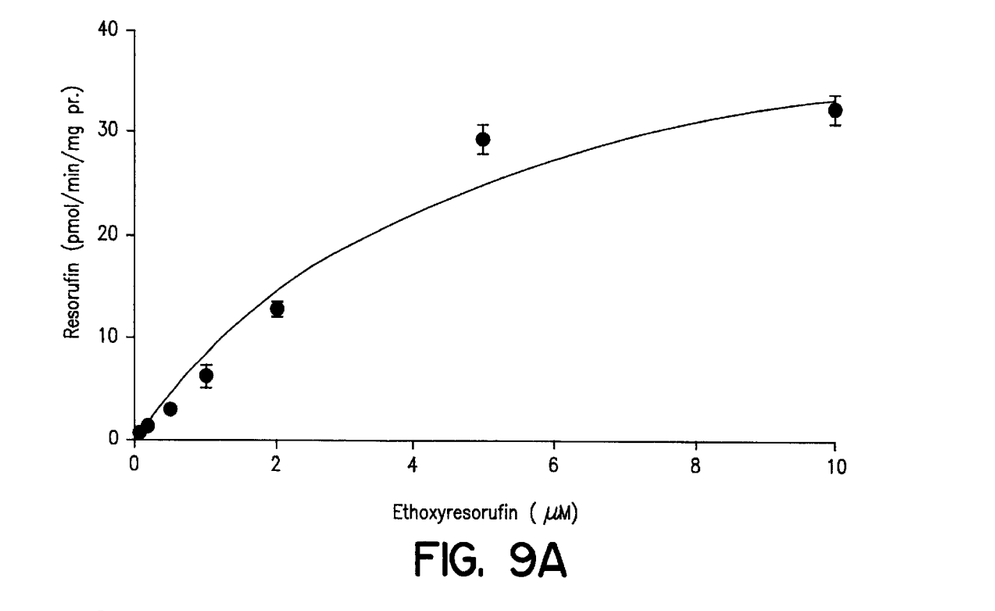
FIG. 9 presents two line graphs which depict the relationship between (a) velocity of resorufin formation and concentrations of ethoxyresorufin; and (b) velocity of DCF formation and concentrations of ethoxyresorufin during CYP1A2-mediated metabolism of ethoxyresorufin. Other conditions are described later herein.
Figure 9B:
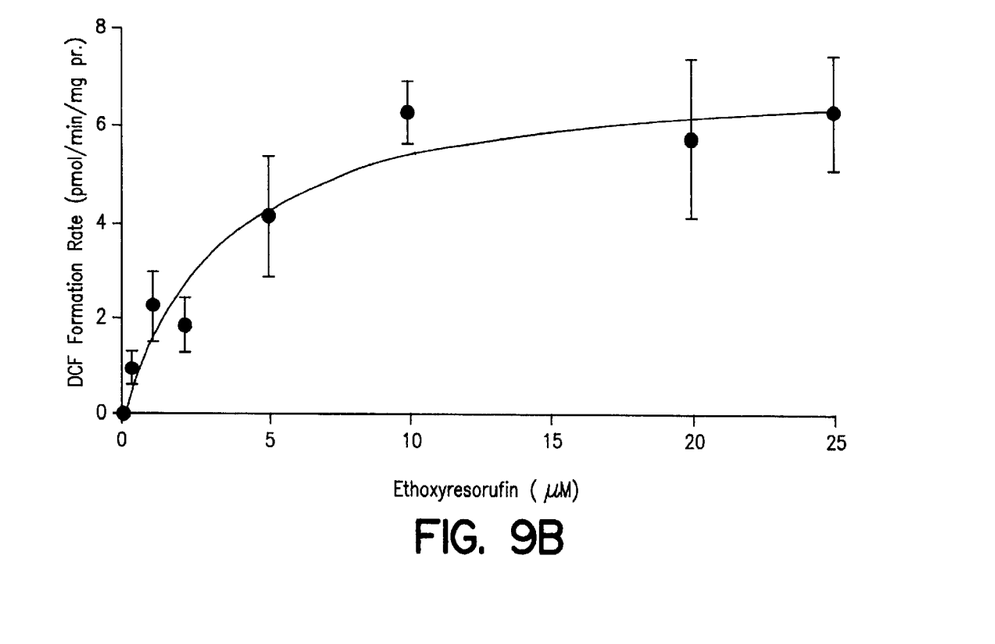

This experiment was conducted to test whether the method of the present invention could be used to measure metabolism of compounds by other CYP isoenzymes in addition to CYP3A4. Metabolism of ethoxyresorufin by CYP1A2 was used as an example. Fluorescent intensity was 39.48, 125.3, and 112.7 for resorufin and 46.94, 92.2 and 146.4 for DCF at 0.5, 5 and 50 μM of ethoxyresorufin, as shown in FIG. 8a. Resorufin formation rate increased proportionally as ethoxyresorufin concentrations increased, and then reached plateau at approximately 10 μM ethoxyresorufin, as shown in FIG. 9a. A similar relationship was observed between formation rate of DCF and concentration of ethoxyresorufin, as shown in FIG. 9b.

Figure 8B:
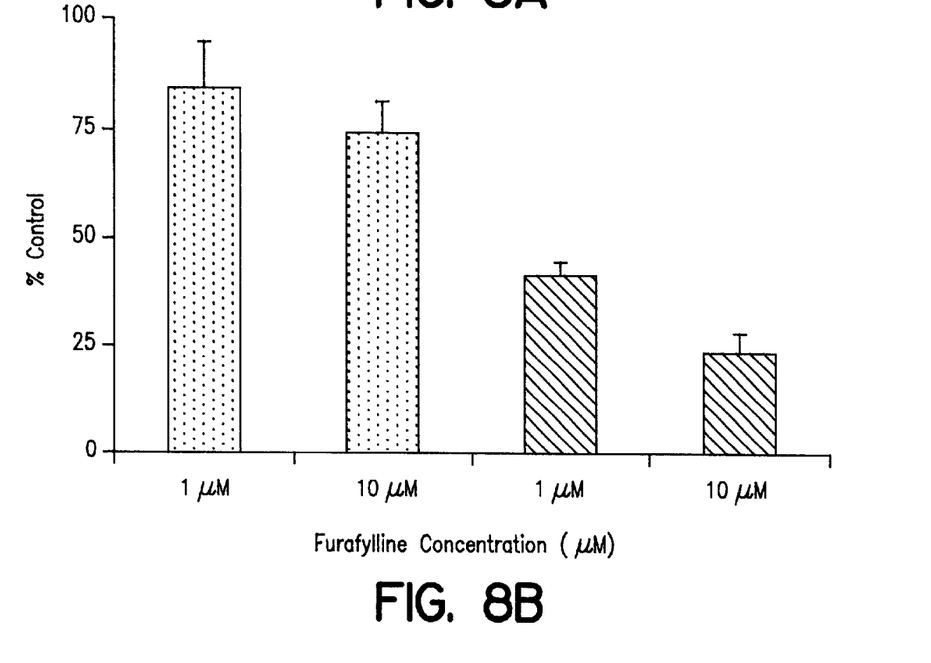

Metabolism kinetic parameters were obtained through analysis of resorufin or DCF formation rate versus concentrations of ethoxyresorufin. The $K_m$ value by measurement of resorufin and DCF was comparable (4.89±1.71 μM versus 3.46±1.07 μM). As shown in FIG. 8b, formation of resorufin was 41.9±2.6% and 23.4±4.3% of the control in the presence of 1 and 10 μM furafylline, respectively. Accordingly, DCF formation also decreased to 83.9±10.2 and 73.9±7.0% of the control.

Discussion of Examples

The novel high throughput screening method/assay for susceptibility to enzymatic metabolism of the present invention is characterized in that it does not require measurement of either the drug molecule or its metabolites. Rather the novel method/assay of the present invention measures or detects an indicator compound (e.g., a fluorescent product, such as DCF) that is converted from an indicator compound precursor (e.g., DCFH-DA, a non-fluorescent probe) during enzymatic metabolism (e.g., CYP-mediated oxidation) of the putative drug molecule.

As particularly described in the Examples, initial experiments were conducted to examine whether DCF could be converted from DCFH-DA using a CYP reaction system comprising CYP3A4OR and testosterone. FIG. 2 demonstrates that DCF was formed during CYP3A4-mediated testosterone oxidation. The formed fluorescent component in the incubation medium had the same excitation and emission maximal wavelengths ($\lambda$ex=503 and $\lambda$em=522 nm in pH 7.4 buffer) as those of the standard DCF. Further experiments showed that DCF was formed from DCFH-DA, as no measurable fluorescent signal was observed at 503 ($\lambda$ex)/522 ($\lambda$em) from an incubation that contained the same components as described previously, except for DCFH-DA. Further, the signals increased with increased DCFH-DA concentration, as depicted in FIG. 3.

The conversion of DCFH-DA to DCF as an indicator of CYP3A4-mediated testosterone metabolism in accordance with the screening method of the present invention was confirmed via a series of experimental results. For example, negligible fluorescent signals were detected for DCF for incubations that were lacking in any of the cofactor NADPH, the metabolizing enzyme CYP3A4, or the substrate testosterone. Negligible DCF formation indicates that no metabolism of testosterone occurred in the incomplete incubation systems. Additionally, no 6$\beta$-OH testosterone, a CYP3A4-specific metabolite of testosterone, was detected by HPLC on the incomplete incubation systems, as shown in Table 1.

In contrast, fluorescence signals were much higher in the incubation systems comprising all the components (testosterone, CYP3A4, NADPH) that are needed for CYP3A4-mediated testosterone biotransformation. These results are also presented in Table 1. Fluorescent signals increased as testosterone concentrations increased, which was also in agreement with a corresponding increase in formation of 6$\beta$-OH testosterone (Table 1). It was noticed that the fluorescent signals from incubations comprising all reagents excluding testosterone but including methanol, a solvent for testosterone, were higher (139±3) than those from incubations without CYP3A4 (29±1) or NADPH (70±11), suggesting that methanol may contribute to increased fluorescent signals. Therefore, it was necessary to subtract the fluorescent signal of the incubations without testosterone comprising the same volume of solvent from that of complete incubation systems in order to calculate DCF formation that was related to CYP3A4-mediated testosterone metabolism.

Ketoconazole and TAO are two well-known CYP3A4 inhibitors (Brian et al., *Biochemistry* 29:11280–11292 (1990); Waxman et al., *Arch. Biochem. Biophys.* 263:424–436 (1988); Halpert et al., *Toxicol. Appl. Pharmacol.* 125:163–175 (1994)). Consistent with the fact that ketoconazole and TAO inhibit CYP3A4-mediated metabolism of testosterone, DCF formation during CYP3A4-mediated metabolism of testosterone (FIG. 6) was also significantly impaired in the presence of these two chemical inhibitors. This observation further supports that DCF formation was associated with CYP3A4-mediated metabolism.

In addition, ketoconazole was observed to be a more potent inhibitor for CYP3A4 as compared to TAO. Indeed, the inhibitory effect of 0.5 $\mu$M ketoconazole, which reduced DCF formation by more than 75%, was similar to that of 10 $\mu$M TAO (FIG. 6). This observation was consistent with the fact that ketoconazole has been shown to be a more potent inhibitor of CYP3A4-mediated metabolism of testosterone as compared to TAO in human liver microsomes (Newton et al., *Drug Metab. Disp.* 23:154–158 (1995)).

Figure 5B:
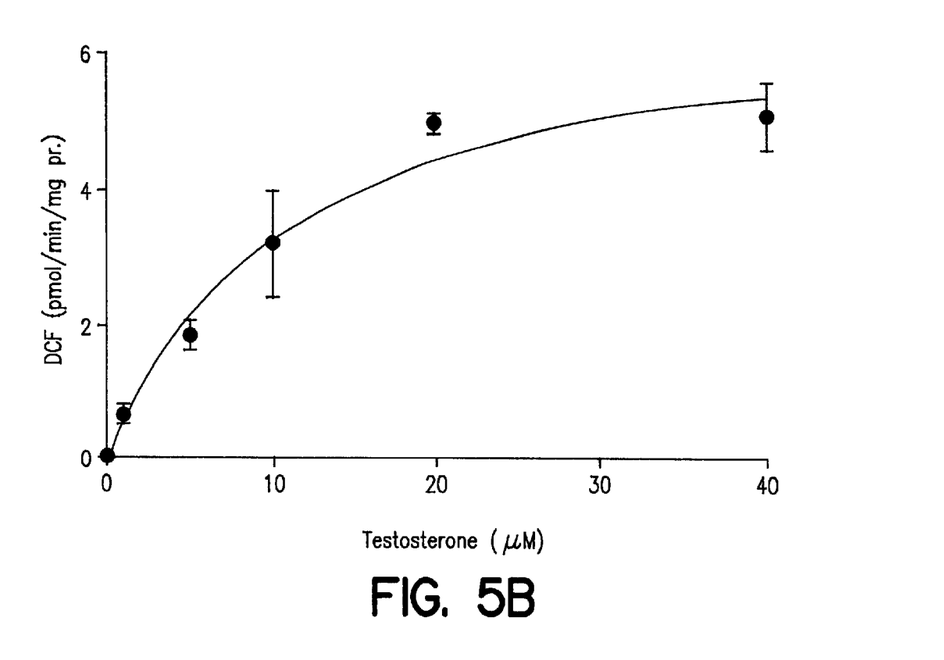

As was observed in the relationship between formation of 6$\beta$-OH testosterone and testosterone concentrations, a plot of DCF formation rate as a function of testosterone concentrations was consistent with Michaelis-Menten kinetic profile (FIG. 5). Thus, it is possible to determine the kinetic parameters such as $K_m$ and $V_{max}$ using formation of DCF. For determination of $V_{max}$, a stoichiometric relationship between formation rates of DCF and those of the reaction products (metabolites) is established.

One of the main objectives of the method of the present invention is the screening of many potential therapeutic agents for susceptibility to enzymatic metabolism in a single effort. Thus, it is preferred that the method be capable of examining metabolic susceptibility of candidate compounds with different metabolic rates and/or affinity. Results from the kinetic study of testosterone, dextromethorphan, benzyloxyresorufin, and phenacetin with respect to CYP3A4-mediated metabolism indicate that the method of the present invention can differentiate compounds with different metabolic properties. For example, the metabolic velocity of testosterone and dextromethorphan mediated by CYP3A4 at 10 min determined with the present method was 2–3 fold higher than that of benzyloxyresorufin, and 10–20 fold greater than that of phenacetin at ~40 $\mu$M concentration of these substrates, as shown in FIG. 10. Likewise, the apparent maximum metabolic velocity ($V_{max}$) of testosterone or dextromethorphan was 6–8 fold greater as compared to that of benzyloxyresorufin (Table 2). Phenacetin is not a known substrate of CYP3A4 and accordingly failed to generate a DCF-related fluorescence signal.

Results from the method of the present invention were in agreement with results from prior art methods. The metabolic parameters for testosterone were determined by measuring 6$\beta$-OH testosterone (Table 1) using prior art HPLC-UV methods, due to the recognized conversion of testosterone to 6$\beta$-OH testosterone by CYP3A4. However, the formation of resorufin from benzyloxyresorufin metabolism mediated by CYP3A4 with fluorescent spectrophotometry method was not determined, most likely due to slow reaction. Therefore, the metabolism kinetic parameters for benxyloxyresorufin were not obtained from the prior art method of direct metabolite measurement. Indeed, Crespi et al., *Anal. Biochem.* 248:188–190 (1997) used benxyloxyresorufin as a probe for CYP3A4 to study inhibition of CYP3A4 by potential CYP3A4 inhibitors and reported that the $V_{max}$ for benzyloxyresorufin by CYP3A4 was 0.31 $min^{-1}$. But, the inventors were not able to convert the unit of $min^{-1}$ to mass of resorufin//min/mg protein due to lack of required information in Crespi et al., *Anal. Biochem.* 248:188–190 (1997).

As for phenacetin, no detectable metabolites were found by prior art HPLC methods under the experimental conditions described above. There was no difference in chromatograms (number and size of peaks) between samples from incubation without NADPH and complete incubation samples with either low (0.5 mg/ml) or high (1 mg/ml) CYP3A4 content and with short (10 min) or long (30 min) incubation time periods. The fact that no detectable metabolites for phenacetin were observed indicates that phenacetin was likely not metabolized by CYP3A4 at all, or at least that the conversion of phenacetin to its potential metabolites was very slow and the metabolites concentration were below the limit of the current UV detection. In either case, the fact that no detectable metabolites were observed from CYP3A4-mediated metabolism of phenacetin as indicated by HPLC analysis was consistent with the negligible amounts of DCF formation observed by fluorescent spectrophotometry.

The results presented in Example 1 above demonstrate that DCF formation was specific to CYP3A4-mediated metabolism and that DCF formation rates were consistent with metabolite formation rates. Therefore, in a preferred embodiment, the method of the present invention may be used to determine susceptibility of candidate drug molecules to CYP3A4-mediated metabolism. Because the method of the present invention is exemplified by a universal characteristic of CYP-mediated metabolism, i.e. production of ROS, the method is also applicable to other CYP isoenzymes in addition to CYP3A4, which is the most abundant CYP isoenzyme in human, as described in Shimada and Guengerich, *Proc. Natl. Acad. Sci. USA* 86:462–465 (1989).

The wide ranging applicability of the method of the present invention is further supported by the results observed with the CYP1A2-mediated metabolism of ethoxyresorufin described in Example 2. CYP1A2 is another major P450 isoenzyme which almost accounts for 15% of total CYPs in human, as described in Estabrook, *FASEB J.* 10:202–204 (1996). As was observed in the results from CYP3A4-mediated metabolism of testosterone, DCF formation was also specific to CYP1A2-mediated ethoxyresorufin metabolism. DCF formation increased as concentration of ethoxyresorufin increased, which was consistent with increased formation of resorufin, metabolite of ethoxyresorufin (FIG. 7a). Furafylline, a mechanism-based inhibitor of CYP1A2, inhibited CYP1A2-mediated metabolism of ethoxyresorufin. Formation of resorufin in the presence of 1 and 10 $\mu$M furafylline reduced to 30% and 25% of the control. Likewise, DCF formation also declined in the presence of furafylline though the magnitude of decrease in DCF formation was not as great as that of resorufin (FIG. 7b).

In summary, a preferred embodiment of the method of the present invention relies on measurement of a fluorescent product (DCF) formation, which is generated by utilizing a fraction of ROS formed during CYP-mediated metabolism. The results presented above indicate that the preferred embodiment of the method of the present invention was valid for both CYP3A4- and CYP1A2-mediated metabolism, and thus can be applied to all other CYP isoenzymes. Since the method of the present invention does not require measurement of metabolites or the parent drug molecules, it can be used as a universal assay for susceptibility to CYP-mediated metabolism that is amenable to high throughput screening. Such an assay can accelerate drug discovery and development tremendously by reducing the time and expense associated with examining candidate compounds for susceptibility to enzymatic metabolism.

REFERENCES

The references listed below as well as all references cited in the specification are incorporated herein by reference to the extent that they supplement, explain, provide a background for or teach methodology, techniques and/or compositions employed herein.

Bass et al., *J. Immunol.* 130:1910–1917 (1983).
Bernhardt, *Rev. Physiol. Biochem. Pharmacol.* 127:138–221 (1995).
Boelsterli et al., *Hepatology* 18: 1154–1161 (1993).
Brian et al., *Biochemistry* 29:11280–11292 (1990).
Crespi et al., *Anal. Biochem.* 248:188–190 (1997).
Estabrook, *FASEB J.* 10:202–204 (1996).
Ghosh et al., *Molecular Cell. Biochem.* 166:35–44 (1997).
Gillette et al., *J. Pharmacol. Exp. Ther.* 119:532–540 (1957).
Halpert et al., *Toxicol. Appl. Pharmacol.* 125:163–175 (1994).
Hildebrandt and Roots, *Arch. Biochem. Biophy.* 171:385–397 (1975).
Knobeloch et al., *J. Appl. Toxicol.* 10:1–5 (1990).
LeBel et al., *Chem. Res. Toxicol.* 5:227–231 (1992).
Lee et al., *Arch. Biochem. Biophy.* 319:157–167 (1995).
Newton et al., *Drug Metab. Disp.* 23:154–158 (1995).
Parkinson, *Toxicol. Pathol.* 24:45–57 (1996).
Shen et al., *Free Radic. Biol. Med.* 21:139–146 (1996).
Shimada and Guengerich, *Proc. Natl. Acad. Sci. USA* 86:462–465 (1989).
Staudt et al., *Eur. J. Biochem.* 46:99–106 (1974).
U.S. Pat. No. 5,478,723.
U.S. Pat. No. 5,786,191.
Waxman et al., *Arch. Biochem. Biophys.* 263:424–436 (1988).

It will be understood that various details of the invention may be changed without departing from the scope of the invention. Furthermore, the foregoing description is for the purpose of illustration only, and not for the purpose of limitation—the invention being defined by the claims.

What is claimed is:

1. A method of screening a candidate compound for susceptibility to metabolism by a selected enzyme, the method comprising the steps of:

(a) providing a candidate compound suspected of being susceptible to metabolism by a selected enzyme;

(b) mixing the candidate compound, an indicator compound precursor and the selected enzyme, wherein a primary metabolic activity of the enzyme produces a chemical species in a side reaction;

(c) producing the chemical species in the side reaction at a rate proportional to the primary metabolic activity of the enzyme if the candidate compound undergoes the primary metabolic activity of the enzyme, whereby a fraction of the chemical species reacts with indicator compound precursor to produce an indicator compound;

(d) detecting the indicator compound, the detection of the indicator compound indicating the susceptibility of the candidate compound to metabolism by the enzyme.

2. The method of claim 1, wherein the chemical species produced in the side reaction by the primary metabolic activity of the enzyme comprises a reactive oxygen species.

3. The method of claim 1, wherein the indicator compound precursor is selected from the group consisting of a fluorogenic compound, a calorimetric compound, a chemiluminescent compound and combinations thereof.

4. The method of claim 1, wherein steps (a) and (b) are carried out in at least one well of a multi-well plate.

5. The method of claim 1, further comprising screening a plurality of candidate compounds simultaneously for susceptibility to metabolism by a selected enzyme.

6. The method of claim 5, wherein steps (a) and (b) are carried out in multiple wells of a multi-well plate.

7. A method of screening a candidate compound for susceptibility to metabolism by a cytochrome P450 enzyme, the method comprising the steps of:

(a) providing a candidate compound suspected of being susceptible to metabolism by a cytochrome P450 enzyme;

(b) mixing the candidate compound, a cytochrome P450 enzyme and an indicator compound precursor, wherein a primary metabolic activity of the cytochrome P450 enzyme produces a chemical species in a side reaction;

(c) producing the chemical species in the side reaction at a rate proportional to the primary metabolic activity of the enzyme if the candidate compound undergoes the primary metabolic activity of the cytochrome P450 enzyme, whereby a fraction of the chemical species reacts with indicator compound precursor to produce an indicator compound; and (d) detecting an indicator compound, the detection of the indicator compound indicating the susceptibility of the candidate compound to metabolism by the cytochrome P450 enzyme.

8. The method of claim 7, wherein the cytochrome P450 enzyme is selected from the group consisting of CYP1A2, CYP2C9, CYP2C19, CYP2D6, CYP3A4 and combinations thereof.

9. The method of claim 7, wherein the cytochrome P450 enzyme comprises a human cytochrome P450 enzyme.

10. The method of claim 9, wherein the human cytochrome P450 enzyme is selected from the group consisting of CYP1A2, CYP2C9, CYP2C19, CYP2D6, CYP3A4 and combinations thereof.

11. The method of claim 7, wherein the chemical species produced in the side reaction by the primary metabolic activity of the cytochrome P450 enzyme comprises a reactive oxygen species.

12. The method of claim 7, wherein the indicator compound precursor is selected from the group consisting of a fluorogenic compound, a colorimetric compound and combinations thereof.

13. The method of claim 7, wherein steps (a) and (b) are carried out in at least one well of a multi-well plate.

14. The method of claim 7, further comprising screening a plurality of candidate compounds simultaneously for susceptibility to metabolism by a selected enzyme.

15. The method of claim 14, wherein steps (a) and (b) are carried out in multiple wells of a multi-well plate.

16. The method of claim 7, further comprising determining an amount of indicator compound formed over a period of time to thereby determine a rate of metabolism of the candidate compound by the cytochrome P450 enzyme.

* * * * *